US00PP11420P

United States Patent [19]

Chamberlin, Sr.

[11] Patent Number: Plant 11,420

[45] Date of Patent: Jun. 20, 2000

[54] PEACH TREE NAMED '88-17'

[75] Inventor: Thomas O. Chamberlin, Sr., Visalia, Calif.

[73] Assignee: Agri Sun Nursery L.L.C., Selma, Calif.

[21] Appl. No.: 09/022,636

[22] Filed: Feb. 12, 1998

[51] Int. Cl.[7] ..... A01H 5/00

[52] U.S. Cl. ..... Plt./197

[58] Field of Search ..... Plt./197, 198

[56] References Cited

U.S. PATENT DOCUMENTS

P.P. 7,248 6/1990 Taylor ..... Plt./197

P.P. 10,085 10/1997 Gerawan ..... Plt./197

*Primary Examiner*—Howard J. Locker

*Assistant Examiner*—Wendy A. Baker

*Attorney, Agent, or Firm*—Burns, Doane, Swecker & Mathis, L.L.P.

[57] ABSTRACT

A new and distinct late-season cultivar of peach tree (i.e., *Prunus persica*) is provided that forms attractive substantially round fruit bearing a very firm flesh. When fully mature, the external surface of the fruit is almost full red. The fruit flesh has a pleasing mild to sweet low acid flavor and is yellow with some red coloration at the pit cavity and streaked throughout the flesh. The fruit also keeps and ships well particularly in view of its inherently very firm consistency. The tree additionally displays a vigorous growth habit.

1 Drawing Sheet

SUMMARY OF THE INVENTION

The present invention is directed to a new and distinct peach (i.e., *Prunus persica*) cultivar that originated as a chance seedling on the property of Agri Sun Nursery L.L.C. located at Selma, Calif. The peach seed used in the planting was of unknown parentage and was obtained from open-pollinated peach trees growing in the same nursery. Further information concerning the origin of the seed is not available. It was the goal of the originator to grow out such seeds in the search of an attractive new peach cultivar that is well suited for commercial peach production under California growing conditions.

The seed that resulted in the formation of the new cultivar of the present invention was planted in the fall and winter of 1986. The first fruit was observed during mid-September 1988 and its attractive and distinctive nature was duly noted. Had my efforts including the growing and study of the seedlings not have led to the discovery and preservation of the new cultivar of the present invention, it would have been lost to mankind.

It was found that the new peach cultivar of the present invention exhibits the following combination of characteristics:

(a) exhibits good vigor, and (b) forms on a regular and productive basis late-maturing substantially round very firm fruit with a substantially flat base and yellow flesh having a mild to sweet low acid flavor with some red coloration at the pit cavity and streaked throughout the flesh at all stages of maturity, and an almost full red external skin surface when fully mature which keeps and ships well.

The new cultivar of the present invention is particularly well suited for producing a quality peach crop that matures late in the season. For instance, when grown at Selma, Calif., harvest dates commonly range from approximately September 19$^{th}$ to September 25$^{th}$. The fruit is near red over its entire surface at such harvest time. The fruit shape is almost full round with a flat base and an almost flat apex area. The apex of the fruit is mostly receded and no fruit apex point has been observed to date. The fruit cannot be considered a full freestone, but the pit is tight and does break free from the flesh with effort. The flesh is considered to be very firm. If not picked, the fruit commonly remains on the tree until after September 30$^{th}$ at Selma, Calif. The fruit has been kept in cold storage for over 30 days and has been found to hold up very well. The fruit flavor at harvest time is very good and can be described as mild to sweet and very low acid in taste.

Asexual reproduction by budding at Selma, Calif. has demonstrated that the characteristics of the new cultivar are firmly fixed and are reliably transferred from one generation to another. Budwood was first collected from the seedling of the new cultivar during the winters of 1988 and 1989. Seedlings were budded on nemaguard rootstock early in the spring of 1989. The first fruit was observed on the resulting trees during mid-September 1992. Subsequent asexual propagation has confirmed the transferability of the results that initially were obtained.

The new cultivar of the present invention has been named '88-17'.

BRIEF DESCRIPTION OF THE PHOTOGRAPH

The accompanying photograph shows specimens of the foliage and fruit of the new cultivar as it begins to approach maturity as depicted in color as nearly true as it is possible to make the same in a color illustration of this character. The plant was grown on nemaguard rootstock at Selma, Calif., and the photograph was obtained as the fruit approached maturity. When fully mature the fruit will exhibit an almost full red appearance on the external surface. The substantially round fruit configuration with a substantially flat base is apparent as is the red coloration streaked throughout and the flesh adjacent to the pit.

DETAILED DESCRIPTION

The following is a detailed description of the new cultivar obtained from first generation budded trees of the new '88-17' cultivar growing on nemaguard rootstock on property of Agri Sun Nursery L.L.C. at Selma, Calif. Color designations are with reference to the Color Name Chart of the Inter-Society Color Council, National Bureau of Standards.

Botanical classification: *Prunus persica,* cv. '88-17'.

Tree:

*Size.*—Typical for peach trees and depending on the nature of shaping and pruning. When budded in early Spring, the typical tree grows to a height of approximately 3 to 6 feet by winter. Beginning in December these trees can be dug, graded, and shipped to farmers for planting commonly at a density of 150 to 1,800 trees Acre. The eventual tree size is influenced by the farming methods utilized.

*Vigor.*—Very vigorous.

*Productivity.*—Very good. Commonly at least 1,500 boxes of fruit each containing approximately 20 to 28 lbs. are produced on mature trees per Acre.

*Regularity of bearing.*—Reliably bears a crop each year.

*Trunk.*—Diameter: typical for peach trees. Commonly approximately 6 to 8 inches on average and is influenced by growing conditions. Surface characteristics: Rough and typical of a peach tree and commonly with approximately 17 to 20 lenticels per square inch. Bark color: gray brown (60 gr. Br.).

Branches:

*Size.*—Typical for peach trees and depending on the nature of shaping and pruning.

*Surface characteristics.*—Typical for peach tree branches. Fruiting branches commonly are 1 to 2 inches in diameter with the size being influenced by pruning and growing conditions.

*Branch angles.*—Considerable variation.

*Color.*—Gray brown (60 gr. Br.).

*Lenticels.*—Small to medium in size and commonly present in a frequency of approximately 17 to 20 per square inch.

Leaves:

*Size.*—Commonly approximately 6 to 7 inches in length and approximately 1⅝ to 1¾ inches in width.

*Configuration.*—Lanceolate.

*Color.*—Dark green (127 gy. 01 G) on the upper surface and light green (120 m.y.G) on the under surface.

*Margins.*—Serrate.

*Petioles.*—Commonly approximately ⅚ to ⅜ inch in length and approximately 1/16 inch in thickness.

*Stem glands.*—Number: commonly one or two pairs depending on the leaf size. Arrangement: positioned on each side of the petiole at the base of the leaf in pairs. Size: primarily medium in size and commonly approximately 1/32 inch in length. Configuration: reniform. Color: brownish-yellow (71 m. oy.).

Flower Buds (observed as pink starts to show at apex of the bud):

*Size.*—Commonly approximately ¼ inch in diameter and approximately ¼ inch in length.

*Petiole.*—Commonly approximately ⅛ inch in length.

*Configuration.*—Substantially round.

*Color.*—Primarily gray green (110 gy. 01).

Flowers:

*Date of bloom.*—approximately March 1$^{st}$ to 6$^{th}$ at Selma, Calif.

*Petal size.*—approximately five in number, ⅞ inch in length and 9/16 inch in width.

*Color.*—Very light pink (7 p. pink).

*Configuration.*—Showy, very sightly elongated.

*Fragrance.*—very light.

*Stem length.*—Commonly approximately ⅛ inch.

Fruit:

*Date of maturity.*—Commonly approximately September 19$^{th}$ or 20$^{th}$ at Selma, Calif.

*Symmetry.*—Substantially round.

*Configuration.*—Possesses wide base and an almost flat apex area.

*Size.* —Commonly approximately 2⅞ to 3½ inches in diameter, approximately 2 7/16 inches transverse in the suture plane, and approximately 2½ to 3½ inches transverse at a right angle to the suture plane. Fruit size varies with growing conditions and the level of fruit thinning (if any). A typical fruit commonly weighs approximately ⅔ lb.

*Suture.*—Very smooth, and the length from the base to the apex commonly is approximately 4¼ to 4¾ inches.

*Stem cavity.*—Commonly substantially round, and approximately 5/16 inch in depth.

*Base.*—Commonly wide and round.

*Apex.*—The apex area commonly is almost flat and lacks a point.

*Pistil point.*—Very receded and very small in size.

Fruit stem:

*Length.*—Commonly approximately ⅜ inch.

*Diameter.*—Commonly approximately ⅛ inch.

Fruit skin:

*Thickness.*—Typical for a peach, smooth, and tenacious to the flesh.

*Color.*—Yellow (71 m. oy.) with a red (16 d. Red) blush as ripening begins, mostly dark red (16 d. Red) when fully mature with some yellow (71 m. oy.) under cast.

*Tendency to crack.*—None.

*Pubescence.*—Very light (as illustrated).

Fruit flesh:

*Consistency.*—Very firm.

*Color.*—Primarily yellow (67 brill. oy) with some red (12 s. Red) adjacent the pit area and streaked throughout the flesh (as illustrated).

*Surface of pit cavity.*—Commonly very rough and dark red in appearance (13 deep Red).

*Juice.*—Medium juicy.

*Aroma.*—Slight.

*Flavor.*—Mild to sweet and very low acid.

*Ripening.*—Substantially even throughout.

*Eating quality.*—Very good, sweet to mild peach flavor, very low acid, and not too crisp.

Stone:

*Degree of freedom.*—Not full-free stone, but does not break free of flesh with effort.

*Fibers.*—Not present.

*Size.*—Commonly approximately 1 3/16 inch in length, approximately 1 5/16 inch in width, and approximately 11/16 inch in thickness.

*Color.*—Dark red (17 v.d. Red).

*Form.*—Ovid.

*Base.*—Rounded and approximately 3/16 inch in diameter.

*Apex.*—Pointed.

*Sides.*—Generally rough.

*Ridges.*—Light and commonly approximately 1/16 inch in depth.

*Tendency to split.*—None.

Pollination requirements: Is self-fertile.
Disease resistance: Conventional spraying for the location where grown is recommended.
Use: Fresh market.
Keeping quality: Keeps well in cold storage.
Shipping quality: Handles and ships well in view of inherently firm consistency.

Although the new '88-17' cultivar of peach tree possesses the above-described characteristics as a result of the growing conditions at Selma, Calif., it is to be expected that variations of the usual type and magnitude may appear that are caused by differences in growing conditions, fertilization, pruning, pest control and other horticultural practices when the new cultivar is grown in different environments.

I claim:

1. A new and distinct cultivar of peach tree that exhibits the following combination of characteristics:

(a) exhibits good vigor, and
(b) forms on a regular and productive basis late-maturing substantially round very firm fruit with a substantially flat base and yellow flesh having a mild to sweet low acid flavor with some red coloration at the pit cavity and streaked throughout the flesh at all stages of maturity and an almost full red external skin surface when fully mature which keeps and ships well;

substantially as herein shown and described.

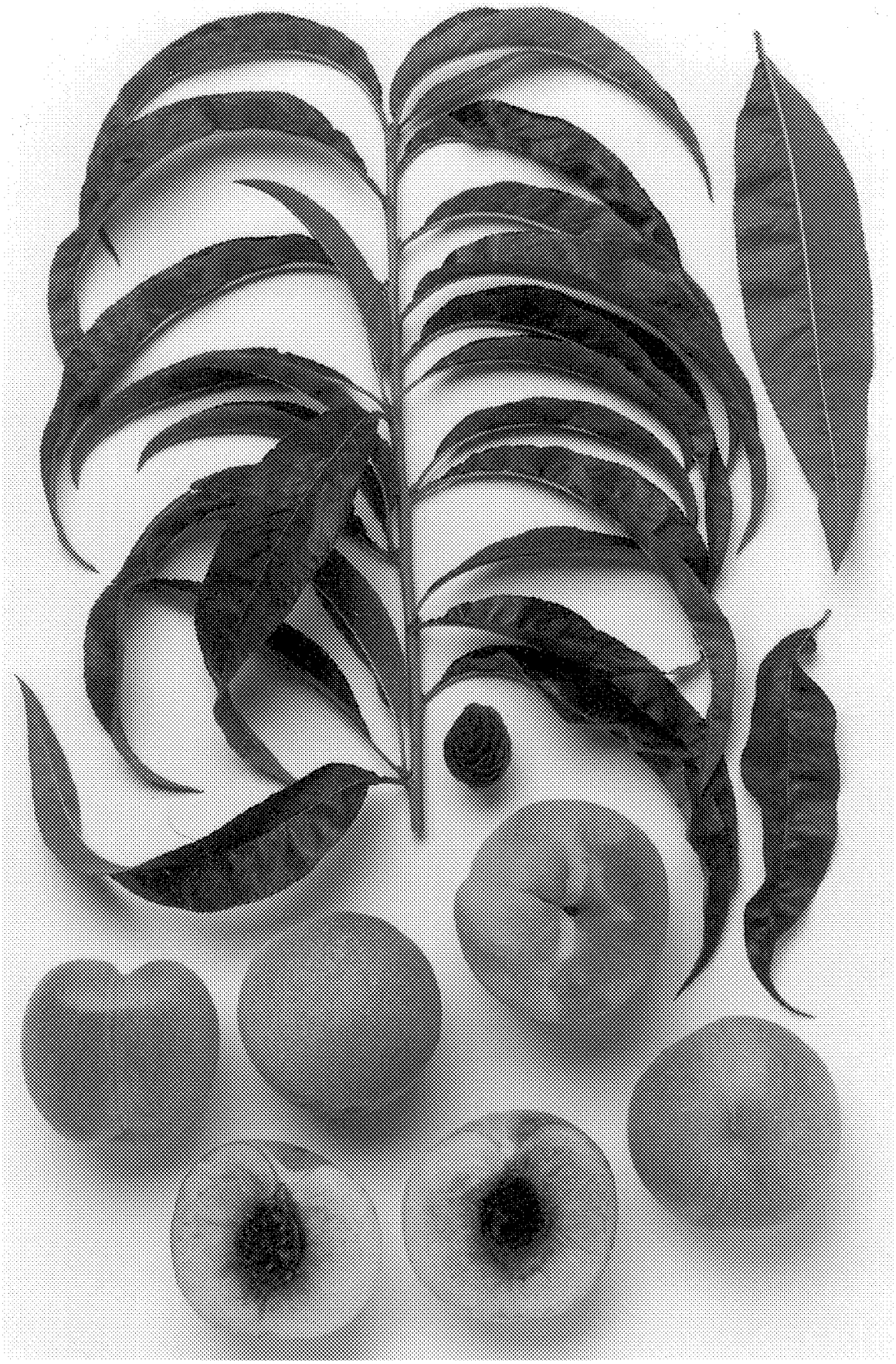

* * * * *